United States Patent
Hotchkiss et al.

(10) Patent No.: US 8,313,789 B2
(45) Date of Patent: Nov. 20, 2012

(54) METHODS OF PROMOTING THE GROWTH OF BENEFICIAL BACTERIA IN THE GUT

(75) Inventors: Arland T. Hotchkiss, Ambler, PA (US); Alberto Nunez, Dresher, PA (US); Robert A. Rastall, Reading (GB); Glenn R. Gibson, Reading (GB)

(73) Assignee: The United States of America, as represented by the Secretary of Agriculture, Washington, DC (US)

(*) Notice: Subject to any disclaimer, the term of this patent is extended or adjusted under 35 U.S.C. 154(b) by 268 days.

(21) Appl. No.: 12/787,771

(22) Filed: May 26, 2010

(65) Prior Publication Data

US 2010/0316766 A1 Dec. 16, 2010

Related U.S. Application Data

(60) Provisional application No. 61/268,236, filed on Jun. 10, 2009.

(51) Int. Cl.
*A23L 1/0524* (2006.01)
(52) U.S. Cl. ............. 426/577; 426/2; 426/648; 426/658
(58) Field of Classification Search ............. 426/2, 648, 426/658, 577
See application file for complete search history.

(56) References Cited

U.S. PATENT DOCUMENTS

2004/0175444 A1* 9/2004 Baik et al. ............. 424/729
2009/0022849 A1 1/2009 Clifford et al.
2009/0186833 A1 7/2009 Kunz et al.

OTHER PUBLICATIONS

J.P. Guggenbichler et al., Acidic oligosaccharides from natural sources block adherence of *Escherichia coli* on uroepithelial cells, Pharm Pharmacol Lett 7 (1997) 1: 35-38.
K. Manderson et al., In Vitro Determination of Prebiotic Properties of Oligosaccharides Derived from an Orange Juice Manufacturing By-Product Stream, Applied and Environmental Microbiology, vol. 71, No. 12, Dec. 2005, p. 8383-8389.
M.A.H.M. Al-Tamimi et al., In vitro fermentation of sugar beet arabinan and arabino-oligosaccharides by the human gut microflora, Journal of Applied Microbiology 100 (2006) p. 407-414.
Katrien M.J. Van Laere et al, Fermentation of Plant Cell Wall Derived Polysaccharides and Their Corresponding Oligosaccharides by Intestinal Bacteria, J. Agric. Food Chem., 2000, 48, p. 1644-1652.
G. Mandalari et al., In vitro evaluation of the prebiotic activity of a pectic oligosaccharide-rich extract enzymatically derived from bergamot peel, Appl Microbiol Biotechnol (2007) 73, p. 1173-1179.

* cited by examiner

*Primary Examiner* — Helen F Heggestad
(74) *Attorney, Agent, or Firm* — John D. Fado; G. Byron Stover

(57) ABSTRACT

A method of promoting the growth of beneficial bacteria in the gut of a human in need thereof, which involves administering to a human a composition containing an effective amount of Ara-(1-5)-(Ara)$_n$-(1-5)-Ara as a prebiotic, where n=0-18.

8 Claims, 3 Drawing Sheets

METHODS OF PROMOTING THE GROWTH OF BENEFICIAL BACTERIA IN THE GUT

REFERENCE TO RELATED APPLICATION

This application claims the benefit of U.S. Provisional Application No. 61/268,236, filed 10 Jun. 2009, which is incorporated herein by reference in its entirety.

BACKGROUND OF THE INVENTION

The present invention relates to methods of promoting the growth of beneficial bacteria in the gut of a human in need thereof, which involves administering to a human a composition containing an effective amount of Ara-(1-5)-(Ara)$_n$-(1-5)-Ara (n=0-18, preferably 0-13) as a prebiotic.

The human gastrointestinal tract is a highly complex microbial ecosystem which has been shown to be remarkably stable (Zoetendal, E. G., et al., Applied and Environmental Microbiology, 64: 3854-3859 (1998)). Many different approaches have been used to modulate the gut flora in a way that is beneficial to host health (Bielecka, M., et al., Food Research International, 35: 125-131 (2002); Steer, T., et al., Nutrition Research Reviews, 13: 229-254 (2000)). These include the addition of living microorganisms to food (probiotics), the addition of food ingredients or dietary fibre to selectively stimulate beneficial bacteria within the host (prebiotics), and a combination of both probiotics and prebiotics (synbiotics). The usual targeted outcome is an increase in the numbers of lactobacilli and bifidobacteria. As an alternative to the addition of live bacteria to the diet, prebiotics have been defined as non-digestible food ingredients that selectively stimulate the growth and/or activity of one or a limited number of bacteria in the colon, and thus improves host health (Gibson, G. R., and M. B. Roberfroid, Journal of Nutrition, 125: 1404-1412 (1995)). All current prebiotics are resistant to the digestive process as they have to reach the colon intact in order to be able to be fermented by the beneficial bacteria lactobacilli and bifidobacteria. The bifidogenic nature of a number of prebiotics has been confirmed in vivo in human feeding studies (Saavedra, J. M., and A. Tschernia, British Journal of Nutrition, 87: s241-s246 (2002); Tuohy, K. M., et al., British Journal of Nutrition, 86: 341-348 (2001); Tuohy, K. M., et al., Microbial Ecology in Health and Disease, 14: 165-173 (2002). These include inulin, fructo-oligosaccharides (FOS), galacto-oligosaccharides (GOS), and lactulose.

We have found that orange pectic oligosaccharides (POS) are rich in arabino-oligosacchrides and these oligosaccharides may be used as a prebiotic.

SUMMARY OF THE INVENTION

In accordance with the present invention there is provided methods of promoting the growth of beneficial bacteria in the gut of a human in need thereof, which involves administering to a human a composition containing an effective amount of Ara-(1-5)-(Ara)$_n$-(1-5)-Ara (n=0-18, preferably 0-13) as a prebiotic.

DETAILED DESCRIPTION OF THE INVENTION

Figure 1:
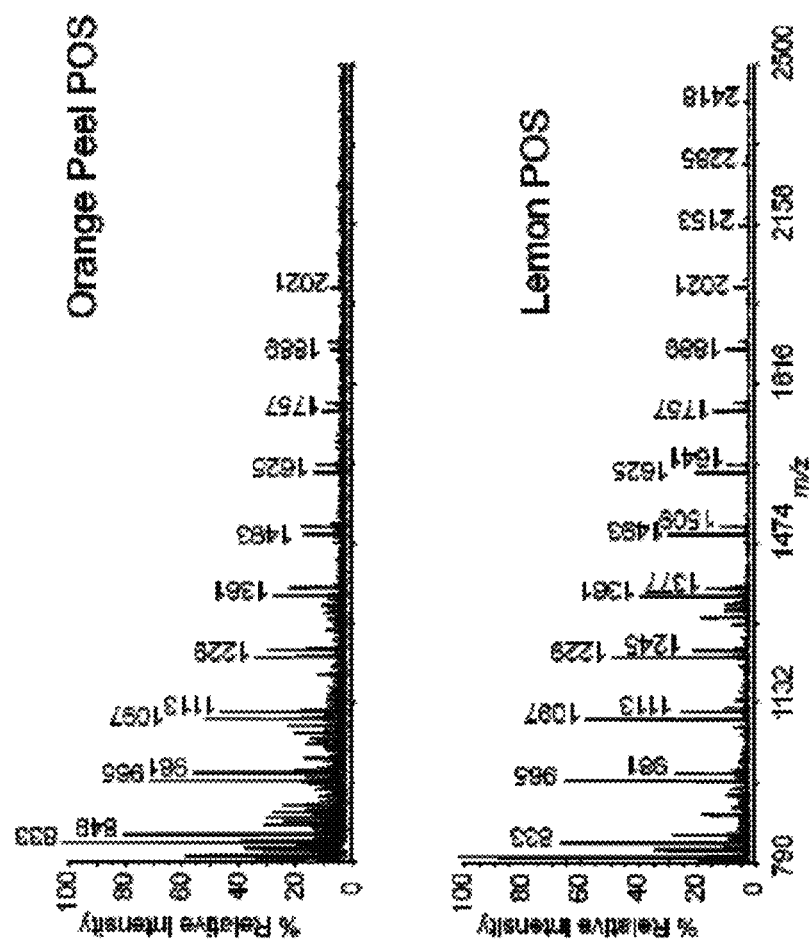
FIG. 1 shows matrix-assisted laser desorption/ionization mass spectrometry with automated tandem time of flight fragmentation of selected ions (MALDI-TOF MS) of orange peel POS (pectic oligosaccharides) and lemon POS as described below.

The present invention is directed to methods of improving the health of a mammal, preferably a human by the ingestion of arabino-oligosaccharides (Ara-(1-5)-(Ara)$_n$-(1-5)-Ara where n=0-18, preferably 0-13). The methods according to the present invention will improve the health of a human by the oral consumption of arabino-oligosaccharides.

In one aspect of the present invention the oral consumption of arabino-oligosaccharides promotes the growth of beneficial gut bacteria.

In another aspect of the present invention the oral consumption of arabino-oligosaccharides promotes the growth of beneficial gut bacteria and reduces the growth of harmful bacteria.

In the context of the present invention beneficial bacteria means those which do not excrete metabolic products that are detrimental to health. Some beneficial bacteria may produce compounds, like vitamins, which are positive to health. They may also be able to inhibit pathogens and are likely to be saccharolytic.

In the context of the present invention harmful bacteria means those which produce toxic products and may also have the ability to cause cell destruction by invasive capacities. Some toxic products produced by harmful bacteria may act locally in the gut and/or have systemic effects.

The invention may be applied to a wide range of compositions comprising arabino-oligosaccharides. Compositions may be in the form of liquids, semi-solids or solids. Compositions may be dairy-based such as yoghurts. Compositions are suitably in the form of beverages. In the context of this invention, the term beverage encompasses ready to drink liquid forms as well as concentrates and powder formulations for dissolution. Ready to drink beverages may be still or carbonated.

The present inventors have found that the prebiotic effect of arabino-oligosaccharides (Ara-(1-5)-(Ara)$_n$-(1-5)-Ara) is particularly pronounced at concentrations of about 0.1—about 10% weight % (e.g., 0.1-10 weight %), preferably about 0.1—about 1 weight % (e.g., 0.1-1 weight %).

The present invention is also particularly suitable for fermented and non-fermented dairy-based products such as yoghurts, fromage frais and milk based beverages.

Compositions of the present invention may be unsweetened or sweetened with sugar or intense sweeteners such as saccharine, aspartyl phenyl alanyl methyl ester, or other non-sugar sweeteners. Compositions may also contain other conventional additives such as flavourings, colourings, stabilisers etc.

Compositions according to the present invention may also contain probiotic and prebiotic mixtures.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Materials and Methods. Test Carbohydrates: Fructo-oligosaccharides (Raftilose P95) and inulin were obtained from Orafti (Tienen, Belgium) and starch from Sigma (Poole, UK). Individual arabino-oligosaccharides with degree of polymerization (DP) of 4 to 8 were purchased from Megazyme (Wicklow, Ireland). All other chemicals were purchased from BDH (Poole, UK) except $MgSO_4.7H_2O$ and L-cysteine HCl which were obtained from Sigma (Poole, Dorset, UK). Orange peel POS was extracted using the procedure reported by Manderson et al. (Manderson, K., et al., Appl. Environ. Microbiol. 71: 8383-8389 (2005)). Lemon peel POS was a gift from Obipektin (Bischofszell, Switzerland). The lemon peel POS was produced from the liquid remaining after hot acid-extraction of lemon peel and isopropyl alcohol precipitation of pectin. Following evaporation of the alcohol, the solution was pumped through a 10,000 MWCO ultrafiltration membrane and lyophilized. POS 2 was also produced from lemon peel that was enzymatically-extracted and the pectin produced was depolymerised further with enzymes. POS1, POS 2, POS TC, MCP 1 and MCP 2 were gifts from EcoNugenics (Santa Rosa, Calif.). The mushroom preparation was according to Wu et al. (Wu, D., et al., J. Nutr. 137: 1472-1477 (2007)).

Oligosaccharide analysis: Monosaccharide analysis by high-performance anion-exchange chromatography with pulsed amperometric detection (HPAEC-PAD) following methanolysis was performed according to the procedure reported by Zhao et al. (Zhao, Z. Y., et al., Alternative Therapies, 14: 34-38 (2008)). Unhydrolysed oligosaccharides were also separated by HPAEC-PAD according to the procedure reported by Rhoades et al. (Rhoades, J., et al., J. Food Protect., 71: 2272-2277 (2008)). Glycosyl linkage GC-MS analysis was performed following preparation of per-O-methylated alditol acetates according to the procedure reported by Domozych et al. (Domozych, D. S., et al., Protoplasma, 230: 99-115 (2007)). KDO content was determined according to the procedure reported by Yoo et al. (Yoo, S.-H., et al., Food Hydrocolloids, 20: 62-67 (2003)).

Matrix-assisted laser desorption/ionization mass spectrometry with automated tandem time of flight fragmentation of selected ions (MALDI-TOF/TOF) of oligosaccharides were acquired with a 4700 Proteomics Analyzer mass spectrometer (Applied Biosystems, Framingham, Mass.) in the positive reflectron mode. Spectra were obtained by averaging 1000 and 2500 acquired spectra in the MS and MS/MS mode, respectively. Collision induced dissociation (CID) with air at an approximately $1 \times 10^{-6}$ Torr; at 1 keV acceleration voltage was used for obtaining the MS/MS spectra for selected oligosaccharides. Conversion of TOF to mass (Da) for the monoisotopic ions, $[M+Na]^+$, was based on calibration of the instrument with a peptide standard calibration kit (Applied Biosystems). Oligosaccharides samples (3-5 mg) were dissolved in 1 mL of water and cleaned with CarboPrep 90 graphitized carbon cartridges, 3 mL, 250 mg (Restek, Bellefonte, Pa.). The cartridges were first conditioned by passing 3 ml of acetonitrile:water (50:50) and then washed 4 times with 3 mL of water. After conditioning, the oligosaccharide solution was passed through the graphitized carbon cartridge, washed 3 times with 3 mL of water and the water wash was discarded. The oligosaccharides were eluted with 1 mL of acetonitrile:water (30:70), 0.1% TFA. From this solution, 2 µL were mixed with 10 µl of a solution of 2,5-dihydroxy benzoic acid (10 mg/mL in acetonitrile:water (50:50), 0.1% TFA), and spotted onto a MALDI plate for analysis.

Faecal batch culture fermentation: Five 280 ml glass fermenter vessels were filled with 180 ml of a pre-reduced sterile medium containing 2 g/l peptone water, 2 g/l yeast extract, 0.1 g/l NaCl, 0.04 g/l $K_2HPO_4$, 0.04 g/l $KH_2PO_4$, 0.01 g/l $MgSO_4.7H_2O$, 0.01 g/l $CaCl_2.2H_2O$, 2 g/l $NaHCO_3$, 0.5 g/l L-cysteine HCl, 0.5 g/l bile salts, 4 ml resazurin 0.05 g/l, 10:1 vitamin $K_1$, 2 ml Tween 80, and 10 ml haemin. The medium was adjusted to pH 7.0 and continuously sparged with oxygen free nitrogen (15 mL/min). A 10% (w/v) faecal slurry from three healthy donors was prepared using pre-reduced 0.1 M phosphate buffered saline (pH 7.0) and then mixed in a stomacher (model 6041, Steward Scientific, UK) for 120 sec. Each vessel was inoculated with 20 ml of the slurry and 2 g of carbohydrate. Fermenters were maintained at 37° C. and duplicate samples removed after 0, 5, 10 and 24 h for the enumeration of bacteria and short-chain fatty acid analysis (Olano-Martin, E., et al., J. Appl. Microbiol., 93: 505-511 (2002); Wang, X., and G. R. Gibson, J. Appl. Bacteriol., 75: 373-380 (1993))). Fermentations were run on three separate occasions with a different donor.

Fluorescent in situ hybridization (FISH): Changes in human faecal bacterial populations were assessed by FISH with 16S rRNA probes. These 16S rRNA probes, specific for predominant classes of the gut microflora (bacteroides, bifidobacteria, clostridia, and lactobacilli/enterococci), were manufactured and tagged with fluorescent markers. The probes used were Bif164 (Langendijk et al., Appl. Environ. Microbiol., 61: 3069-3075 (1995)), Bac303 (Manz, Microbiology, 142: 1097-1106 (1996)), His150 (Franks, Appl. Environment. Microbiol., 64: 3336-3345 (1998)), and Lab158 (Harmsen et al., Microbial Ecology Health Disease, 11: 3-12 (1996)). The nucleic acid stain 4'6-diamidino-2-phenylindole (DAPI) was used for total bacterial counts. Fermentation samples were diluted and fixed overnight in 4% paraformaldehyde at 4° C. in a ratio of 1:3 (v/v). These cells were then washed with phosphate buffered saline (0.1 M, pH 7.0), resuspended in 150 µl PBS+150 µl ethanol, and stored at −20° C. for a minimum of 1 h. The cell suspension was then added to the hybridization mixture: 4.78 g/l Tris-HCL (30 mM), 79.69 g/l NaCl (1.36 M), 15 ml 10% SDS solution pH 7.2 with 4 M HCl and filtered through 0.2 µm filter (Millipore, Watford, UK). Hybridization was carried out at appropriate temperatures for the probes. Subsequently, the hybridization mix was vacuum filtered (Millipore, Watford, UK) and the filter mounted on a microscope slide and examined using fluorescence microscopy, such that the bacterial groups could be enumerated (Ryecroft et al., J. Appl. Microbiol., 91: 878 (2001)).

Results and Discussion: POS consisted of arabino se-rich oligosaccharides with varying amounts of glucose and galacturonic acid (Table 1). Minor amounts (0.17%) of 2-keto-3-deoxyoctonic acid (KDO) were present in orange POS. The KDO level was lower than that reported for modified citrus pectin (MCP) (Eliaz, I., et al., Phytother. Res., 20: 859-864 (2006)) and suggested that orange peel POS may only contain 3% rhamnogalacturonan II. POS contained an overabundance of galacturonic acid compared to the number of rhamnose residues and there was roughly a 10:1 arabinose:rhamnose ratio. Partially methyl-esterified oligogalacturonic acids were present and were significantly detected following saponification. Therefore, the rhamnogalacturonan I structure in POS may be highly localized.

We reported that the glucose in orange POS was free glucose carried over from the peel (Manderson, K., et al., Appl. Environ. Microbiol., 71: 8383-8389 (2005)). When orange POS was purified with a graphitized carbon cartridge (O POS C in Table 1), much of the free glucose was removed and the galacturonic acid level rose. The glycosyl-linkage composition of orange POS also confirmed the presence of free glucose (T-Glc in Table 2). A 5-linked arabinan structure with every other arabinose branched at the 3-position was observed. A highly branched 6-linked galactan that appears to be similar to type II arabinogalactan (6-linked with every other galactose branched at the 3-position and single arabinose residues attached to the 6-position of 3-linked galactan) was also present in orange POS (Table 2). The presence of terminal arabinose supported the presence of arabinogalactan in which galactan oligosaccharide chains were decorated with single arabinose residues.

The lemon POS was also arabinose-rich and contained a relatively high level of glucose apparently left-over from the peel. The enzymatic extraction and depolymerisation pectin from lemon peel (POS 2) produced an arabinose-rich POS with little glucose and almost a 10:1 arabinose:rhamnose ratio. Apparently, the production process for POS 2 must have removed the free glucose associated with the other POS fractions.

Based on monosaccharide, oligosaccharide and glycosyl-linkage composition, POS was a mixture of homogalacturonan, rhamnogalacturonan I, rhamnogalacturonan II, arabinan and type II arabinogalactan oligosaccharides. Therefore, we turned to MALDI-TOF MS analysis to determine if there was a dominant oligosaccharide structure present in POS. Both orange and lemon POS had [M+Na]$^+$ ions consistent with a pentose repeat structure (FIG. 1). The orange POS contains pentose repeat oligosaccharides up to DP 15 ([M+Na]$^+$=2021) and up to DP 20 was detected in lemon POS ([M+Na]$^+$2681, not shown in FIG. 1). These MALDI-TOF MS spectra were only observed following graphitized carbon cartridge purification of orange and lemon POS. It is possible that free glucose may have inhibited ionization of POS in the MALDI matrix. Since levels of xylose were relatively low in POS compared to arabinose, the structure of these oligosaccharides was tentatively assigned as Ara-(1-5)-(Ara)$_n$-(1-5)-Ara. It was not possible to determine if the oligosaccharides were branched with MALDI-TOF MS; however, the glycosyl-linkage analysis of orange POS demonstrated that half of the arabinose residues are branched at the 3-position.

Figure 2:
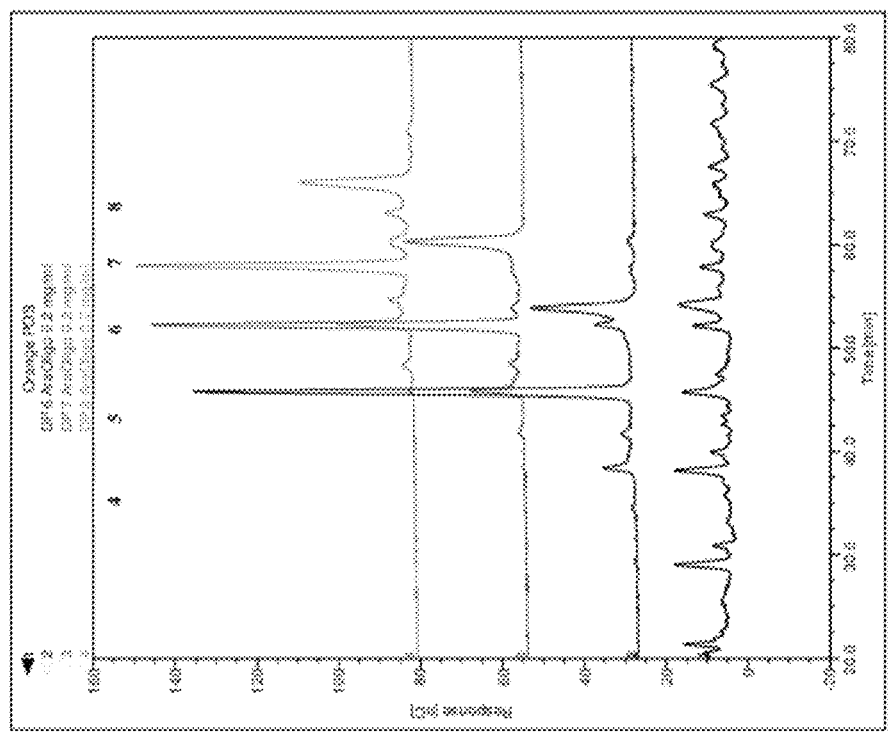
FIG. 2 shows high-performance anion-exchange chromatography with pulsed amperometric detection (HPAEC-PAD) of orange POS compared to arabino-oligosaccharide standards (Megazyme, Wicklow, Ireland) as described below.

HPAEC-PAD was used to confirm that these pentose repeat oligosaccharides were arabino-oligosaccharides. While not identified in Rhoades et al. (2008), besides the peak at 40.6 min in FIG. 1, the remaining series of peaks co-eluted with arabino-oligosaccharide standards. Following saponification (30 min, pH 12), all of the major peaks in orange POS co-eluted with arabino-oligosaccharide standards (FIG. 2). The arabino-oligosaccharide standards contained a major peak (DP labeled above peaks) and secondary peaks which presumably represented branched forms. For example, the peak at 54.2 min could represent an arabino-oligosaccharide with a linear chain of five 5-linked arabinose residues and a sixth arabinose attached at the 3-position to an arabinose in the main linear chain. Most of the secondary peaks in the arabino-oligosaccharide standards were also present in orange POS. HPAEC-PAD analysis also confirmed that arabino-oligosaccharides were the dominant oligosaccharide series in POS. No other peaks were as abundant.

We extracted an arabinose-rich POS from sugar beet pulp that had arabinan (T-Ara, 3-Ara, 5-Ara, 3,5-Ara linkages detected) and arabinogalactan (T-Ara, 3,6-Gal linkages detected) structure. However, the sugar beet POS did not have in vitro prebiotic activity. The significant difference between the orange POS and sugar beet POS was that the sugar beet POS was dominated by homogalacturonan oligosaccharides rather than arabino-oligosaccharides. HPAEC-PAD analysis revealed a series of 4,5-unsaturated oligogalacturonic acids with DP up to at least 30 as the dominant oligosaccharides present. An unsaturated hexuronic acid repeat structure was also detected in sugar beet POS by MALDI-TOF MS following graphitized carbon cartridge treatment. No pentose repeat was detected in sugar beet POS MALDI-TOF MS spectra. The major glycosyl linkage in sugar beet POS was 4-linked galacturonosyl (7× greater peak area than 5-Ara). Therefore, while homogalacturonan can be part of the POS structure, it is clearly not responsible for in vitro prebiotic functionality.

Figure 3:
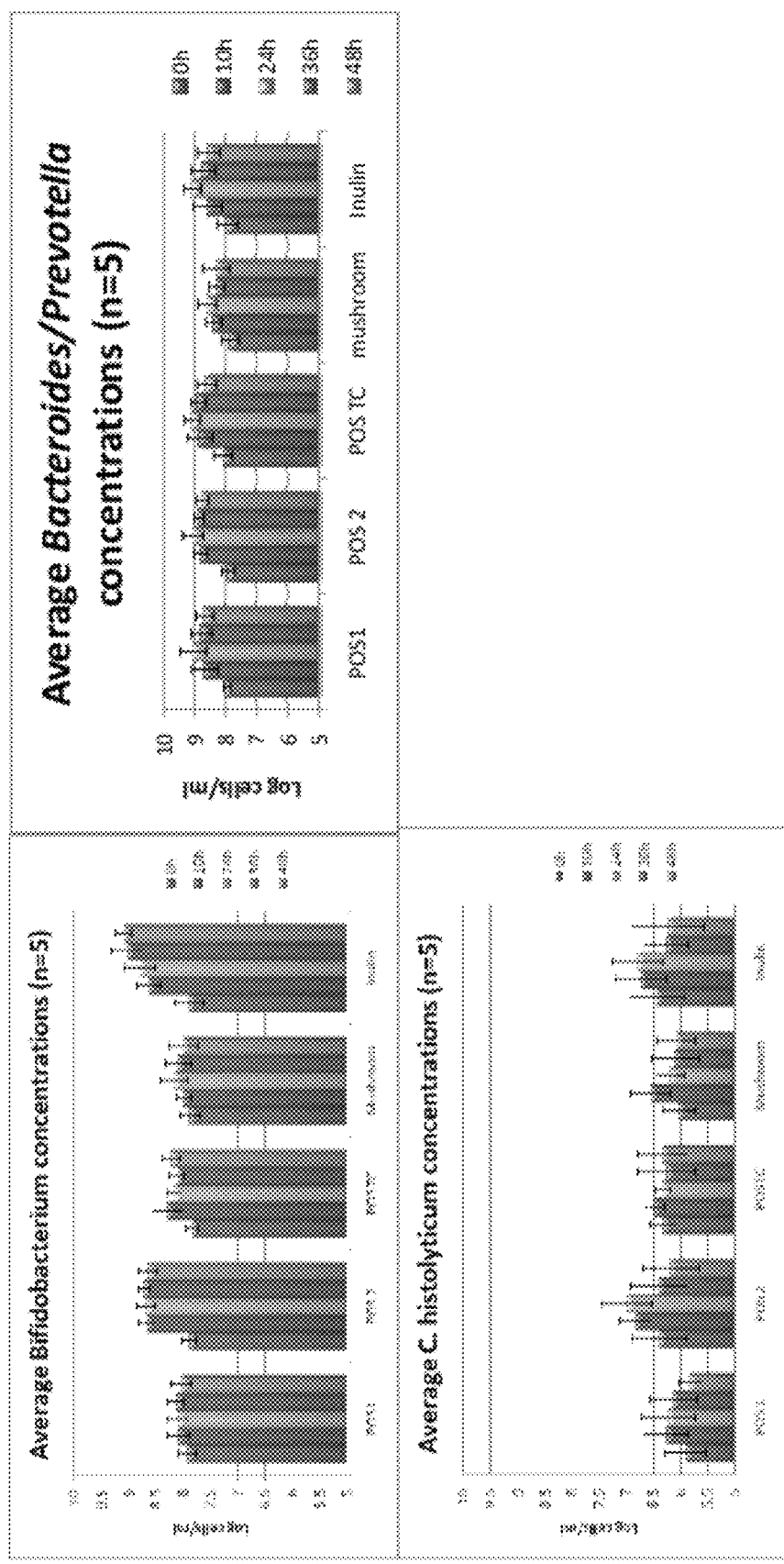
FIG. 3 shows fluorescent in situ hybridization (FISH) analysis of mixed batch fecal cultures treated with POS compared to a mushroom preparation and inulin as described below.

Lemon POS is bifidogenic. In a preliminary study using one fecal donor, the FISH raw data demonstrated that Bifidobacteria counts were surprisingly elevated when lemon POS and POS 2 were included in the mixed batch fecal cultures (Table 3). Since the lemon POS was an experimental sample in limited supply and POS 2 was a commercial sample available in larger quantities, we repeated the in vitro prebiotic analysis with POS 2. Using five fecal donors, FISH analysis of mixed batch fecal cultures indicated that POS 2 surprisingly had strong in vitro prebiotic activity (FIG. 3). Inulin surprisingly produced a greater in vitro bifidogenic response in this analysis. Based on this analysis, POS 2 represented a viable POS sample with in vitro prebiotic activity. Generally in vitro prebiotic activity is known to predict in vivo prebiotic activity.

All of the references cited herein, including U.S. patents, are incorporated by reference in their entirety. Also incorporated by reference in their entirety are the following references: Al-Tamimi, M. A. H. M., et al., J. Appl. Microbiol., 100: 407-414 (2005); Eliaz, I., et al., Phytother. Res., 20: 859-864 (2006); Franks, Appl. Environment. Microbiol., 64: 3336-3345 (1998); Harmsen et al., Microbial Ecology Health Disease, 11: 3-12 (1996); Hotchkiss, A. T, et al., Symbiotic matrices derived from plant oligosaccharides and polysaccharides, In: N. Parris, L. Liu, C. Song and V. P. Shastri (eds.), New delivery systems for controlled drug release from naturally occurring materials, ACS Symposium Series 992, American Chemical Society, Washington, D.C., pp. 69-77 (2008); Langendijk et al., Appl. Environ. Microbiol., 61: 3069-3075 (1995); Mandalari, G., et al., Appl. Microbiol. Biotechnol., 73: 1173-1179 (2007); Manderson, K., et al., Appl. Environ. Microbiol., 71: 8383-8389 (2005); Manz, Microbiology, 142: 1097-1106 (1996); Olano-Martin, E., et al., J. Appl. Microbiol., 93: 505-511 (2002); Ryecroft et al., J. Appl. Microbiol., 91: 878 (2001); Van Laere, K. M. J., et al., J. Agric. Food Chem., 48: 1644-1652 (2000); Voragen, A. G. J., et al., Potential of pectins as structurally complex polymers, 229th American Chemical Society Meeting, San Diego, Calif., CELL 93 (2005); Wang, X., and G. R. Gibson. J. Appl. Bacteriol., 75: 373-380 (1993); Wu, D., et al., J. Nutr., 137: 1472-1477 (2007); United States Patent Application 20090022849.

Thus, in view of the above, the present invention concerns (in part) the following:

Ara-(1-5)-(Ara)$_n$-(1-5)-Ara as a prebiotic, where n=0-18 or n=0-13.

A method of promoting the growth of beneficial bacteria in the gut of a human in need thereof, which comprises (consists essentially of or consists of) administering to said human a composition comprising (consisting essentially of or consists of) an effective amount (an effective beneficial bacteria growth promoting amount) of Ara-(1-5)-(Ara)$_n$-(1-5)-Ara as a prebiotic, where n=0-18.

The above method, wherein n=0-13.

The above method, wherein said composition contains about 0.1—about 10% weight % of Ara-(1-5)-(Ara)$_n$-(1-5)-Ara.

The above method, wherein said composition contains about 0.1—about 1% weight % of Ara-(1-5)-(Ara)$_n$-(1-5)-Ara.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Monosaccharide Composition (mole %) of Pectic Oligosaccharide (POS) Fractions

| Product | Glucose | Arabinose | Galactose | Xylose | Rhamnose | Fucose | Galacturonic Acid | Glucuronic Acid |
|---|---|---|---|---|---|---|---|---|
| O POS | 48.3 | 20.4 | 6.4 | 3.6 | 2.2 | 0.2 | 18.8 | 0.1 |
| O POS C | 13.6 | 27.0 | 4.4 | 2.6 | 1.9 | 0.2 | 49.6 | 0.8 |
| L POS | 32.6 | 44.9 | 4.1 | 7.1 | 7.9 | 0.6 | 1.3 | 1.5 |
| POS 2 | 3.8 | 33.7 | 6.9 | 2.0 | 3.5 | 0.3 | 49.2 | 0.7 |

O POS = orange pectic oligosaccharides,
O POS C = O POS fraction eluted from a graphitized carbon cartridge,
L POS = lemon pectic oligosaccharides,
POS 2 = lemon pectic oligosaccharides; determined by HPAEC-PAD of monosaccharides following methanolysis.

TABLE 2

GC-MS Glycosyl Linkage Composition of Orange POS

| Glycosyl-Linkage | T-Glc | T-Araf | T-Galp | 5-Araf | 3,5-Araf | 6-Galp | 3,6-Galp | 2,6-Galp | 4,6-Galp |
|---|---|---|---|---|---|---|---|---|---|
| Peak Area | 17,843 | 4536 | 3848 | 13,663 | 6500 | 11,720 | 6000 | 6000 | 8000 |

TABLE 3

Raw data from FISH analysis of mixed batch fecal cultures treated with POS (n = 1)

| | Lemon POS | POS 1 | POS 2 | MCP1 | MCP2 | Mushroom |
|---|---|---|---|---|---|---|
| DAPI | | | | | | |
| 0 | 8.6828 | 8.8688 | 8.6148 | 8.6411 | 8.722 | 8.7473 |
| 5 | 8.5844 | 8.6844 | 8.7217 | 8.7798 | 8.885 | 8.7627 |
| 10 | 8.6302 | 9.0228 | 8.8732 | 8.9837 | 8.9057 | 8.8062 |
| 24 | 8.6674 | 8.7606 | 8.8235 | 9.0463 | 8.8616 | 8.6966 |
| BIF | | | | | | |
| 0 | 8.08 | 8.08 | 8.08 | 8.08 | 8.08 | 8.08 |
| 5 | 8.73 | 8.46 | 8.36 | 8.20 | 8.28 | 8.30 |
| 10 | 8.20 | 8.16 | 8.11 | 8.34 | 8.24 | 8.02 |
| 24 | 8.55 | 8.18 | 8.56 | 8.31 | 7.97 | 8.43 |
| BAC | | | | | | |
| 0 | 8.19 | 8.19 | 8.19 | 8.19 | 8.19 | 8.19 |
| 5 | 8.18 | 8.55 | 8.66 | 8.55 | 8.27 | 8.31 |
| 10 | 8.42 | 8.64 | 8.36 | 8.59 | 8.33 | 8.36 |
| 24 | 7.99 | 8.70 | 8.60 | 8.68 | 8.65 | 8.65 |
| EREC | | | | | | |
| 0 | 7.90 | 7.90 | 7.90 | 7.90 | 7.90 | 7.90 |
| 5 | 7.66 | 7.84 | 7.64 | 7.55 | 7.70 | 7.71 |
| 10 | 7.61 | 7.89 | 7.97 | 7.73 | 7.68 | 7.84 |
| 24 | 7.74 | 7.92 | 7.87 | 7.99 | 7.80 | 7.71 |
| LAB | | | | | | |
| 0 | 7.62 | 7.62 | 7.62 | 7.62 | 7.62 | 7.62 |
| 5 | 7.64 | 7.44 | 8.13 | 7.17 | 7.45 | 7.88 |
| 10 | 7.26 | 7.60 | 7.89 | 7.47 | 7.94 | 7.85 |
| 24 | 7.73 | 7.76 | 7.94 | 8.06 | 7.97 | 7.34 |

DAPI = Total Bacteria,
BIF = Bifidobacteria,
BAC = Bacteroides,
EREC = Eubacteria,
LAB = Lactobacilli

We claim:

1. A method of promoting the growth of beneficial bacteria in the gut of a human in need thereof, which comprises administering to said human a composition comprising an effective amount of a pectic oligosaccharide fraction containing Ara-(1-5)-(Ara)$_n$-(1-5)-Ara as a prebiotic, where n =0-18; wherein said pectic oligosaccharide fraction has an arabinose to rhamnose ratio of 5.7 to 14.2.

2. The method according to claim 1, wherein n =0-13.

3. The method according to claim 1, wherein said composition contains about 0.1 about 10% weight % of Ara-(1-5)-(Ara)$_n$-(1-5)-Ara.

4. The method according to claim 1, wherein said composition contains about 0.1- about 1% weight % of Ara-(1-5)-(Ara)$_n$-(1-5)-Ara.

5. The method according to claim 1, wherein said pectic oligosaccharide fraction has an arabinose to rhamnose ratio of about 10:1.

6. The method according to claim 1, wherein said pectic oligosaccharide fraction contains 3.8 mole % glucose, 33.7 mole % arabinose, 6.9 mole % galactose, 2.0 mole % xylose, 3.5 mole % rhamnose, 0.3 mole % fucose, 49.2 mole % galacturonic acid, and 0.7 mole % glucuronic acid.

7. The method according to claim 1, wherein said pectic oligosaccharide fraction is isolated from orange peel or lemon peel.

8. The method according to claim 1, wherein said pectic oligosaccharide fraction is isolated from lemon peel.

* * * * *